United States Patent
Shi (10) Patent No.: US 9,289,452 B2
(45) Date of Patent: Mar. 22, 2016

(54) CONSISTENT CALCIUM CONTENT BONE ALLOGRAFT SYSTEMS AND METHODS

(71) Applicant: AlloSource, Centennial, CO (US)

(72) Inventor: Yaling Shi, Larkspur, CO (US)

(73) Assignee: AlloSource, Centennial, CO (US)

( * ) Notice: Subject to any disclaimer, the term of this patent is extended or adjusted under 35 U.S.C. 154(b) by 15 days.

(21) Appl. No.: 14/200,353

(22) Filed: Mar. 7, 2014

(65) Prior Publication Data
US 2014/0255489 A1    Sep. 11, 2014

Related U.S. Application Data

(60) Provisional application No. 61/774,036, filed on Mar. 7, 2013.

(51) Int. Cl.
*A61K 35/32*    (2015.01)
*A61L 27/36*    (2006.01)

(52) U.S. Cl.
CPC ............ *A61K 35/32* (2013.01); *A61L 27/3608* (2013.01); *A61L 2430/02* (2013.01)

(58) Field of Classification Search
CPC . A61K 35/32; A61L 2430/02; A61L 27/3608
See application file for complete search history.

(56) References Cited

U.S. PATENT DOCUMENTS

| | | |
|---|---|---|
| 4,627,853 A | 12/1986 | Campbell et al. |
| 5,073,373 A | 12/1991 | O'Leary et al. |
| 5,284,655 A | 2/1994 | Bogdansky et al. |
| 5,314,476 A | 5/1994 | Prewett et al. |
| 5,397,353 A | 3/1995 | Oliver et al. |
| 5,405,390 A | 4/1995 | O'Leary et al. |
| 5,439,684 A | 8/1995 | Prewett et al. |
| 5,507,810 A | 4/1996 | Prewettet et al. |
| 5,507,813 A | 4/1996 | Dowd et al. |
| 5,510,396 A | 4/1996 | Prewett et al. |
| 5,531,791 A | 7/1996 | Wolfinbarger |
| 5,676,146 A | 10/1997 | Scarborough |
| 5,707,962 A | 1/1998 | Chen et al. |

(Continued)

FOREIGN PATENT DOCUMENTS

| | | |
|---|---|---|
| WO | 2011019361 | 2/2011 |
| WO | 2012135205 | 10/2012 |

(Continued)

OTHER PUBLICATIONS

Sterigraft [online] retrieved on Aug. 6, 2015 from:http://www.bonebank.com/files/43.pdf; Nov. 14, 2012; 1 page.*
International Search Report and Written Opinion mailed Aug. 15, 2014 for International Patent Application No. PCT/US2014/021856 filed Mar. 7, 2014, all pages.

(Continued)

*Primary Examiner* — Ernst V Arnold
(74) *Attorney, Agent, or Firm* — Kilpatrick Townsend & Stockton LLP (57) ABSTRACT

Embodiments of the present invention provides bone graft compositions, and methods for their use and manufacture. A bone graft composition may include a first amount of non-demineralized cancellous bone. The composition may further include a second amount of demineralized cancellous bone. The composition may also include a third amount of demineralized cortical bone. The non-demineralized cancellous bone, the demineralized cancellous bone, and the demineralized cortical bone may be obtained from the same cadaveric donor.

14 Claims, 4 Drawing Sheets

(56) References Cited

U.S. PATENT DOCUMENTS

| | | | |
|---|---|---|---|
| 5,749,874 A | 5/1998 | Schwartz | |
| 5,769,899 A | 6/1998 | Schwartz et al. | |
| 5,788,941 A | 8/1998 | Dalmasso et al. | |
| 5,895,426 A | 4/1999 | Scarborough et al. | |
| 5,948,428 A | 9/1999 | Lee et al. | |
| 5,972,368 A | 10/1999 | McKay | |
| 6,090,998 A | 7/2000 | Grooms et al. | |
| 6,180,606 B1 | 1/2001 | Chen et al. | |
| 6,189,537 B1 | 2/2001 | Wolfinbarger | |
| 6,200,347 B1 | 3/2001 | Anderson et al. | |
| 6,214,369 B1 | 4/2001 | Grande | |
| 6,294,041 B1 | 9/2001 | Boyce et al. | |
| 6,315,795 B1 | 11/2001 | Scarborough et al. | |
| 6,340,477 B1 | 1/2002 | Anderson | |
| 6,371,988 B1 | 4/2002 | Pafford et al. | |
| 6,436,138 B1 | 8/2002 | Dowd | |
| 6,464,983 B1 | 10/2002 | Grotendorst | |
| 6,478,825 B1 | 11/2002 | Winterbottom et al. | |
| 6,482,231 B1 | 11/2002 | Abatangelo | |
| 6,482,233 B1 | 11/2002 | Aebi et al. | |
| 6,511,509 B1 | 1/2003 | Ford et al. | |
| 6,576,015 B2 | 6/2003 | Geistlich et al. | |
| 6,616,698 B2 | 9/2003 | Scarborough | |
| 6,652,593 B2 | 11/2003 | Boyer, II et al. | |
| 6,685,626 B2 | 2/2004 | Wironen | |
| 6,696,073 B2 | 2/2004 | Boyce et al. | |
| 6,716,245 B2 | 4/2004 | Pasquet et al. | |
| 6,743,574 B1 | 6/2004 | Wolfinbarger et al. | |
| 6,746,484 B1 | 6/2004 | Liu et al. | |
| 6,753,181 B2 | 6/2004 | Atala | |
| 6,800,480 B1 | 10/2004 | Bodnar et al. | |
| 6,805,713 B1 | 10/2004 | Carter et al. | |
| 6,855,169 B2 | 2/2005 | Boyer et al. | |
| 6,902,578 B1 | 6/2005 | Anderson et al. | |
| 6,911,045 B2 | 6/2005 | Shimp | |
| 6,911,212 B2 | 6/2005 | Gertzman et al. | |
| 7,018,412 B2 | 3/2006 | Ferreira et al. | |
| 7,048,765 B1 | 5/2006 | Grooms et al. | |
| 7,115,146 B2 | 10/2006 | Boyer, II et al. | |
| 7,132,110 B2 | 11/2006 | Kay et al. | |
| 7,163,691 B2 | 1/2007 | Knaack et al. | |
| 7,172,629 B2 | 2/2007 | McKay | |
| 7,241,874 B2 | 7/2007 | Thorne | |
| 7,297,540 B2 | 11/2007 | Mitrani | |
| 7,316,822 B2 | 1/2008 | Binette et al. | |
| 7,323,011 B2 | 1/2008 | Shepard et al. | |
| 7,335,381 B2 | 2/2008 | Malinin | |
| 7,371,409 B2 | 5/2008 | Petersen et al. | |
| 7,498,040 B2 | 3/2009 | Masinaei et al. | |
| 7,582,309 B2 | 9/2009 | Rosenberg et al. | |
| 7,608,113 B2 | 10/2009 | Boyer et al. | |
| 7,622,562 B2 | 11/2009 | Thorne et al. | |
| 7,648,676 B2 | 1/2010 | Mills et al. | |
| 7,662,185 B2 | 2/2010 | Alfaro et al. | |
| 7,753,963 B2 | 7/2010 | Boyer et al. | |
| 7,785,634 B2 | 8/2010 | Borden | |
| 7,807,458 B2 | 10/2010 | Schiller | |
| 7,811,608 B2 | 10/2010 | Kay et al. | |
| 7,815,926 B2 | 10/2010 | Syring et al. | |
| 7,837,740 B2 | 11/2010 | Semler et al. | |
| 7,875,296 B2 | 1/2011 | Binette et al. | |
| 7,879,103 B2 | 2/2011 | Gertzman et al. | |
| 7,883,511 B2 | 2/2011 | Fernyhough | |
| 7,931,692 B2 | 4/2011 | Sybert et al. | |
| 8,002,813 B2 | 8/2011 | Scarborough et al. | |
| 8,002,837 B2 | 8/2011 | Stream et al. | |
| 8,025,896 B2 | 9/2011 | Malaviya et al. | |
| 8,039,016 B2 | 10/2011 | Drapeau et al. | |
| 8,137,702 B2 | 3/2012 | Binette et al. | |
| 8,163,549 B2 | 4/2012 | Yao et al. | |
| 8,167,943 B2 | 5/2012 | Carter et al. | |
| 8,197,474 B2 | 6/2012 | Scarborough et al. | |
| 8,202,539 B2 | 6/2012 | Behnam et al. | |
| 8,268,008 B2 | 9/2012 | Betz et al. | |
| 8,292,968 B2 | 10/2012 | Truncale et al. | |
| 8,328,876 B2 | 12/2012 | Behnam et al. | |
| 8,343,229 B2 | 1/2013 | Coale | |
| 8,389,017 B1 | 3/2013 | Starling et al. | |
| 8,399,010 B2 | 3/2013 | McKay | |
| 8,403,991 B2 | 3/2013 | Ullrich, Jr. et al. | |
| 8,409,623 B2 | 4/2013 | Shim et al. | |
| 8,435,566 B2 | 5/2013 | Behnam et al. | |
| 8,496,970 B2 | 7/2013 | Binette et al. | |
| 8,506,632 B2 | 8/2013 | Ganem et al. | |
| 8,551,176 B2 | 10/2013 | Ullrich, Jr. et al. | |
| 8,563,040 B2 | 10/2013 | Marchosky | |
| 8,574,825 B2 | 11/2013 | Shelby et al. | |
| 8,585,766 B2 | 11/2013 | Ullrich, Jr. et al. | |
| 8,722,075 B2 | 5/2014 | Shimp et al. | |
| 8,771,368 B2 | 7/2014 | McKay | |
| 8,859,007 B2 | 10/2014 | Carter et al. | |
| 8,992,964 B2 | 3/2015 | Shelby et al. | |
| 8,992,965 B2 | 3/2015 | Behnam | |
| 9,029,077 B2 | 5/2015 | Song et al. | |
| 2004/0043006 A1 | 3/2004 | Badylak et al. | |
| 2004/0156834 A1* | 8/2004 | Slavin et al. | 424/93.71 |
| 2007/0014729 A1 | 1/2007 | Farhat et al. | |
| 2007/0020248 A1 | 1/2007 | Everaerts et al. | |
| 2007/0110820 A1 | 5/2007 | Behnam | |
| 2007/0185231 A1 | 8/2007 | Liu et al. | |
| 2008/0058953 A1 | 3/2008 | Scarborough | |
| 2008/0249632 A1 | 10/2008 | Stone et al. | |
| 2008/0249638 A1 | 10/2008 | Asgari | |
| 2008/0286268 A1 | 11/2008 | Johnson | |
| 2008/0305145 A1 | 12/2008 | Shelby et al. | |
| 2008/0306610 A1 | 12/2008 | Wang et al. | |
| 2009/0053279 A1 | 2/2009 | Badylak et al. | |
| 2009/0155378 A1 | 6/2009 | Behnam et al. | |
| 2009/0202977 A1 | 8/2009 | Ott et al. | |
| 2010/0124776 A1 | 5/2010 | Shi | |
| 2010/0168869 A1 | 7/2010 | Long et al. | |
| 2010/0196333 A1 | 8/2010 | Gaskins et al. | |
| 2010/0241228 A1 | 9/2010 | Syring et al. | |
| 2011/0070271 A1 | 3/2011 | Truncale et al. | |
| 2012/0035276 A1 | 2/2012 | Spievack | |
| 2012/0082704 A1 | 4/2012 | Phillips et al. | |
| 2012/0189707 A1 | 7/2012 | Chun et al. | |
| 2012/0213859 A1 | 8/2012 | Shelby et al. | |
| 2012/0251609 A1 | 10/2012 | Huang et al. | |
| 2012/0259415 A1 | 10/2012 | Van Dyke et al. | |
| 2013/0013068 A1 | 1/2013 | Forsell et al. | |
| 2013/0189338 A1 | 7/2013 | Drapeau et al. | |
| 2013/0287741 A1 | 10/2013 | Stilwell et al. | |
| 2014/0056865 A1 | 2/2014 | Samaniego et al. | |
| 2014/0093543 A1 | 4/2014 | Morreale | |
| 2014/0121772 A1 | 5/2014 | Emerton et al. | |
| 2014/0170232 A1 | 6/2014 | Shelby et al. | |
| 2014/0205674 A1 | 7/2014 | Wei | |
| 2014/0208980 A1 | 7/2014 | Song et al. | |
| 2014/0212471 A1 | 7/2014 | Drapeau et al. | |
| 2014/0212499 A1 | 7/2014 | Cooper et al. | |
| 2014/0220142 A1 | 8/2014 | Song et al. | |
| 2014/0255506 A1 | 9/2014 | Behnam et al. | |
| 2014/0314822 A1 | 10/2014 | Carter et al. | |
| 2014/0342013 A1 | 11/2014 | He et al. | |
| 2015/0004247 A1 | 1/2015 | Carter et al. | |
| 2015/0012107 A1 | 1/2015 | Koford et al. | |
| 2015/0174295 A1 | 6/2015 | Woodell-May et al. | |
| 2015/0182667 A1 | 7/2015 | Guelcher et al. | |
| 2015/0202345 A1 | 7/2015 | Shelby et al. | |
| 2015/0202346 A1 | 7/2015 | Shelby et al. | |
| 2015/0258244 A1 | 9/2015 | Shelby et al. | |

FOREIGN PATENT DOCUMENTS

| | | |
|---|---|---|
| WO | 2012142419 A1 | 10/2012 |
| WO | 2013047936 | 4/2013 |
| WO | 2014/138612 | 9/2014 |

OTHER PUBLICATIONS

Zimmer Dental, "Puros® Cortico-Cancellous Particulate Allograft" [Accessed on Nov. 3, 2015. Retrieved from the internet: http://www.

(56) References Cited

OTHER PUBLICATIONS zimmerdental.com/Products/Regenerative/rg_puPuCorticoCancelPartAllogr.aspx].

Zimmer Dental, "RegenaVate TM Demineralized Bone Matrix" [Accessed on Nov. 3, 2015. Retrieved from the internet: http://www.zimmerdental.com/Products/Regenerative/rg_puRegenaVateDeminBoneMat.aspx.].

International Preliminary Report on Patentability for International Application No. PCT/US2014/021856 filed Mar. 7, 2014, mailed Sep. 17, 2015, 8 pages.

* cited by examiner

CONSISTENT CALCIUM CONTENT BONE ALLOGRAFT SYSTEMS AND METHODS

CROSS-REFERENCES TO RELATED APPLICATIONS

This application is a nonprovisional of, and claims the benefit of priority to, U.S. Provisional Patent Application No. 61/774,036 filed Mar. 7, 2013, the entire content of which is incorporated herein by reference for all purposes.

BACKGROUND OF THE INVENTION

Embodiments of the present invention are directed in general to the field of medical grafts, and in particular to bone graft compositions, and methods of their use and manufacture.

Medical grafting procedures often involve the implantation of autogenous, allograft, or synthetic grafts into a patient to treat a particular condition or disease. The use of musculoskeletal allograft tissue in reconstructive orthopedic procedures and other medical procedures has markedly increased in recent years, and millions of musculoskeletal allografts have been safely transplanted. A common allograft is bone. Typically, bone grafts are reabsorbed and replaced with the patient's natural bone upon healing. Bone grafts can be used in a variety of indications, including neurosurgical and orthopedic spine procedures for example. In some instances, bone grafts can be used to fuse joints or to repair broken bones.

Allograft and autogenous bone are both derived from humans; the difference is that allograft is harvested from an individual (e.g. donor) other than the one (e.g. patient) receiving the graft. Allograft bone is often taken from cadavers that have donated their bone so that it can be used for living people who are in need of it, for example, patients whose bones have degenerated from cancer. Such tissues represent a gift from the donor or the donor family to enhance the quality of life for other people.

Hence, bone graft compositions and methods are presently available and provide real benefits to patients in need thereof. Yet many advances may still be made to provide improved bone graft systems and methods for treating patients. The bone graft systems and treatment and manufacture methods described herein provide further solutions and answers to these outstanding needs.

BRIEF SUMMARY OF THE INVENTION

Bone is composed of organic and inorganic elements. By weight, bone is approximately 20% water. The weight of dry bone is made up of inorganic minerals such as calcium phosphate (e.g. about 65-70% of the weight) and an organic matrix of fibrous protein and collagen (e.g. about 30-35% of the weight). Both mineralized and demineralized bone can be used for grafting purposes.

Embodiments of the present invention encompass bone graft compositions containing mixtures of mineralized and demineralized bone, such that the compositions provide a bone allograft material having consistent calcium content, certain mechanical properties and handling characteristics, and desired biological activities.

In one aspect, embodiments of the present invention encompass composite bone graft materials, and methods for their use and manufacture. An exemplary method of manufacturing a composite bone graft material for administration to a treatment site of a human patient may include selecting a target calcium content or handling characteristic of the bone graft material, selecting a first amount of mineralized (i.e., non-demineralized) donor bone material, selecting a second amount of demineralized donor bone material, and combining the first and second amounts of bone material so as to obtain a bone graft composition having the target calcium content or handling characteristic. In these or other embodiments, the first amount of mineralized donor bone material may be selected based on the target calcium content or handling characteristic. Relatedly, the second amount of demineralized donor bone material may be selected based on the target calcium content or handling characteristic. In some instances, a ratio of the first amount of mineralized donor bone material to the second amount of demineralized donor bone material may be selected based on the target calcium content or handling characteristic. In some embodiments, the donor is an allogeneic cadaveric donor. In some embodiments, the composite bone graft material includes tissue obtained from the patient. In some embodiments, methods may also include combining adult mesenchymal stem cells with the bone material.

In another aspect, embodiments of the present invention may include a bone graft composition. The bone graft composition may include a first amount of non-demineralized cancellous bone, a second amount of demineralized cancellous bone, and a third amount of demineralized cortical bone. The non-demineralized cancellous bone, the demineralized cancellous bone, and the demineralized cortical bone may be obtained from the same cadaveric donor. Non-demineralized bone may be bone that has not contacted any acid and/or has not undergone either a complete or an incomplete demineralization process.

In some embodiments, the first amount of non-demineralized cancellous bone may have particles with sizes selected based on needs of the patient, needs of the physician, or for other reasons. Large particles may be difficult for a physician to handle or to mix. Examples of particle sizes may include between about 0.1 mm and about 9 mm, between about 2 mm and about 8 mm, between about 1 mm and about 7 mm, between about 1 mm and about 6 mm, between about 1 mm and about 5 mm, between about 0.1 mm and about 4 mm, between about 1 mm and about 4 mm, or between about 0.1 mm and about 1 mm in embodiments. The volume of the first amount may be chosen based on desired handling characteristics of the final product and/or the targeted calcium content. For example, the first amount may be between about 30% and about 70%, between about 40% and about 60%, between about 45% and about 55%, between about 48% and about 52%, between about 38% and about 42%, or about 50% of the volume of the bone graft composition. The non-demineralized cancellous bone in the first amount may have a calcium content selected based on handling characteristics or targeted calcium content. For example, the calcium content may be between about 20% and about 25%.

In some embodiments, the second amount of demineralized cancellous bone may include particles having sizes based on needs of the patient, needs of the physician, or for other reasons. Large particles may be difficult for a physician to handle or to mix. Examples of particle sizes may include between about 0.1 mm and about 9 mm, between about 2 mm and about 8 mm, between about 1 mm and about 7 mm, between about 1 mm and about 6 mm, between about 1 mm and about 5 mm, between about 0.1 mm and about 4 mm, between about 1 mm and about 4 mm, or between about 0.1 mm and about 1 mm, or between about 0.5 mm and about 4 mm in embodiments. The second amount of demineralized cancellous bone may include mesenchymal stem cells seeded to the surface of the demineralized cancellous bone. The volume of the second amount may be chosen based on desired handling characteristics of the final product and/or the targeted calcium content. For example, the second amount may be between about 30% and about 70%, between about 40% and about 60%, between about 45% and about 55%, between about 48% and about 52%, between about 38% and about 42%, or about 50% of the volume of the bone graft composition. The calcium content of the demineralized cancellous bone may be based on targeted calcium content or handling characteristics. For example, the calcium content may be between about 0% and about 8%, between about 0% and about 4%, between about 4% and about 6%, between about 0% and about 2%, or about 0% in embodiments.

In these or other embodiments, the third amount of demineralized cortical bone may have particle sizes selected based on needs of the patient, needs of the physician, or for other reasons. Small sizes may be easier for a physician to handle and may more easily fit inside cancellous bone material and not affect the volume of the final composition. For example, particles may have sizes between about 100 µm and 2 mm, between about 1 mm and about 2 mm, between about 120 µm and about 710 µm, or between about 100 µm and 1 mm. Smaller particles may increase biological activity. Cortical bone may contain growth factors, which may aid bone graft treatments. The volume of the third amount may be based on targeted calcium content, growth factor content, or handling characteristics. For example, the third amount may be between about 10% and about 40%, between about 10% and about 30%, between about 15% and about 25%, between about 19% and about 21%, or about 20% of the volume of the bone graft composition in embodiments. The calcium content of the demineralized cortical bone may be based on targeted calcium content or handling characteristics. For example, the demineralized cortical bone in the third amount may have a calcium content between about 0% and about 8%, between about 0% and about 4%, between about 4% and about 6%, between about 0% and about 2%, or about 0% in embodiments.

In these or other embodiments, the bone graft composition may have a calcium content between about 10% and about 19%, between about 10% and about 15%, between about 12% and about 17%, or about 15%. The calcium content of the bone graft composition may be measured by a residual calcium test or other known methods. The demineralized bone material may make up between about 25% and about 75%, between about 50% and about 75%, between about 40% and about 60%, or about 50% of the cancellous bone in the bone graft composition in embodiments. The remainder of the cancellous bone material may be non-demineralized bone material.

In another aspect, embodiments of the present invention may include a method of manufacturing a composite bone graft material for administration to a treatment site of a patient. The method may include selecting a target calcium content or handling characteristic of the composite bone graft material. In these or other embodiments, the method may include selecting a first amount of non-demineralized bone material from a donor, selecting a second amount of demineralized bone material from the donor, and combining the first and second amounts of bone material so as to obtain a bone graft composition having the target calcium content or handling characteristic. The target calcium content may be between about 10% and about 19%, between about 10% and about 15%, between about 12% and about 17%, or about 15% in embodiments. The donor may be a cadaveric donor allogeneic to the patient. The method may include combining bone material from the patient with the first and second amounts of bone material from the donor.

In some embodiments, for the first amount, the non-demineralized bone material may include cancellous bone. The first amount of non-demineralized cancellous bone may have particles with sizes based on needs of the patient, needs of the physician, or for other reasons. Large particles may be more difficult for a physician to handle or to mix. Examples of particle sizes may include between about 0.1 mm and about 9 mm, between about 2 mm and about 8 mm, between about 1 mm and about 7 mm, between about 1 mm and about 6 mm, between about 1 mm and about 5 mm, between about 0.1 mm and about 4 mm, between about 1 mm and about 4 mm, or between about 0.1 mm and about 1 mm in embodiments. The volume of the first amount may be chosen based on desired handling characteristics of the final product or the targeted calcium content. For example, the first amount may be between about 30% and about 70%, between about 40% and about 60%, between about 45% and about 55%, between about 48% and about 52%, between about 38% and about 42%, or about 50% of the volume of the bone graft composition.

In these or other embodiments, for the second amount, the demineralized bone material may include cancellous bone. Particle sizes and volume percentages may be selected based on targeted calcium content or handling characteristics. Examples of particle sizes may include between about 0.1 mm and about 9 mm, between about 2 mm and about 8 mm, between about 1 mm and about 7 mm, between about 1 mm and about 6 mm, between about 1 mm and about 5 mm, between about 0.1 mm and about 4 mm, between about 1 mm and about 4 mm, or between about 0.1 mm and about 1 mm, or between about 0.5 mm and about 4 mm in embodiments. The second amount may be between about 30% and about 70%, between about 40% and about 60%, between about 45% and about 55%, between about 48% and about 52%, between about 38% and about 42%, or about 50% of the volume of the bone graft composition in embodiments.

In embodiments, the method may include selecting a third amount of demineralized donor material. The demineralized donor bone material may include cortical bone. Particles may have sizes between about 100 µm and 2 mm, between about 1 mm and about 2 mm, between about 120 µm and about 710 µm, or between about 100 µm and 1 mm. The volume of the third amount may be based on targeted calcium content, growth factor content, or handling characteristics. For example, the third amount may be between about 10% and about 40%, between about 10% and about 30%, between about 15% and about 25%, between about 19% and about 21%, or about 20% of the volume of the bone graft composition in embodiments. In these or other embodiments, combining the first and second amounts of bone material may include combining the third amount with the first and second amounts.

Prior to the combining step, the method may include seeding the mesenchymal stem cells onto the demineralized bone material. The method may include seeding a stromal vascular fraction onto the demineralized bone material, and the stromal vascular fraction may include mesenchymal stem cells and unwanted cells. In these or other embodiments, the method may include incubating the mesenchymal stem cells on the demineralized bone material for a period of time to allow the mesenchymal stem cells to adhere to the demineralized bone material. The method may include rinsing the seeded demineralized bone material to remove the unwanted cells from the demineralized bone material.

In another aspect, embodiments of the present invention may include a method of treating a bone defect or other ailment in a patient. The method may include administering to the patient a bone graft composition that may include a first amount of non-demineralized cancellous bone, a second amount of demineralized cancellous bone, and a third amount of demineralized cortical bone. The non-demineralized cancellous bone, the demineralized cancellous bone, and the demineralized cortical bone may be obtained from the same cadaveric donor. The bone graft composition may be administered to treat spinal problems. With some spinal problems, the spine may need to be fused. In these or other embodiments, the bone graft composition may be placed in a spine cage, which may be placed between vertebrae. Additionally, the bone graft composition may be used to treat nonunions or critical size defects. In these or other embodiments, the bone graft composition may be applied or administered to the bone defect or surrounding bone.

In yet another aspect, embodiments of the present invention may include a method of manufacturing a composite bone graft material for administration to a treatment site of a patient. The method may include selecting a target calcium content or handling characteristic of the composite bone graft material. In these or other embodiments, the method may include selecting a first amount of non-demineralized bone material that includes cancellous bone from a donor. The first amount may have a first volume equal to about 50% of the composite bone graft material, and the first amount may include particles having sizes between about 0.1 mm and about 9 mm. The method may include selecting a second amount of demineralized bone material that contains cancellous bone from the donor. The second amount may have a second volume equal to about 50% of the composite bone graft material, and the second amount may have particles with sizes between about 0.1 mm and about 9 mm. In these or other embodiments, the method may include selecting a third amount of demineralized cortical bone, where the third amount may have a third volume equal to about 20% of the composite bone graft material. The method may include combining the first amount, second amount, third amount, and adult mesenchymal stem cells so as to obtain a bone graft composition having the target calcium content or handling characteristic.

The above described and many other features and attendant advantages of embodiments of the present invention will become apparent and further understood by reference to the following detailed description when considered in conjunction with the accompanying drawings.

DETAILED DESCRIPTION OF THE INVENTION

Embodiments of the present invention encompass bone graft compositions and methods for their use and manufacture. Bone graft compositions as disclosed herein are provided with selected calcium content and/or handling characteristics. An exemplary manufacturing method may include selecting a target calcium content or handling characteristic of a bone graft composition, selecting a first amount of mineralized bone material, selecting a second amount of demineralized bone material, and combining the first and second amounts of bone material so as to obtain a bone graft composition having the target calcium content or handling characteristic.

Demineralization

Bone contains both mineralized and unmineralized components. For example the osteoid, which can be about 50% of the bone volume, is composed mainly of collagen. The mineralization of osteoid by inorganic mineral salts provides bone with its strength and rigidity. Bone contains several inorganic mineral components, such as calcium phosphate, calcium carbonate, magnesium, fluoride, sodium, and the like. Typical demineralization procedures involve removing such mineral components from bone. Any of a variety of techniques can be used to demineralize bone, including hydrochloric acid treatments, and the like. Demineralized bone matrix (DBM) refers to allograft bone that has had the inorganic mineral removed, leaving behind the organic collagen matrix. The American Association of Tissue Banks typically defines demineralized bone matrix as containing no more than 8% residual calcium as determined by standard methods. In this sense, a fully demineralized bone tissue can be considered to have no more than 8% residual calcium. It has been observed that cells such as mesenchymal stem cells may exhibit an affinity for adhering with demineralized bone.

Cortical Bone

Cortical bone, also known as compact bone, can be found in the outer shell portion of various bones. Cortical bone is typically, dense, hard, strong, and stiff. Cortical bone may include bone growth factors.

Cancellous Bone

Cancellous bone, also known as spongy bone, can be found at the end of long bones. Cancellous bone is typically less dense, softer, weaker, and less stiff than cortical bone.

Mineral Content of Bone

Cortical bone and cancellous bone can be harvested from a donor individual using standard techniques. The mineral or calcium content of the harvested bone may vary. In some cases, cortical bone is about 95% mineralized and cancellous bone is about 35-45% mineralized. In some cases, cortical bone is about 73.2 wt % mineral content, and cancellous bone is about 71.5 wt % mineral content. In some cases, the mineral content of the starting bone material is about 25%, prior to demineralization.

Composite Bone Materials

Embodiments of the present invention encompass bone materials containing various mixtures of mineralized (or non-demineralized bone) combined with demineralized bone. For example, bone compositions may include fully demineralized bone (e.g. cortical and/or cancellous) combined with non-demineralized bone (e.g. cortical and/or cancellous). Non-demineralized bone may be bone that has not undergone any demineralization, including treatment with acid. Demineralized and non-demineralized bone can be combined a certain ratios to provide bone allograft material having consistent calcium content and/or consistent handling characteristics.

Figure 1:
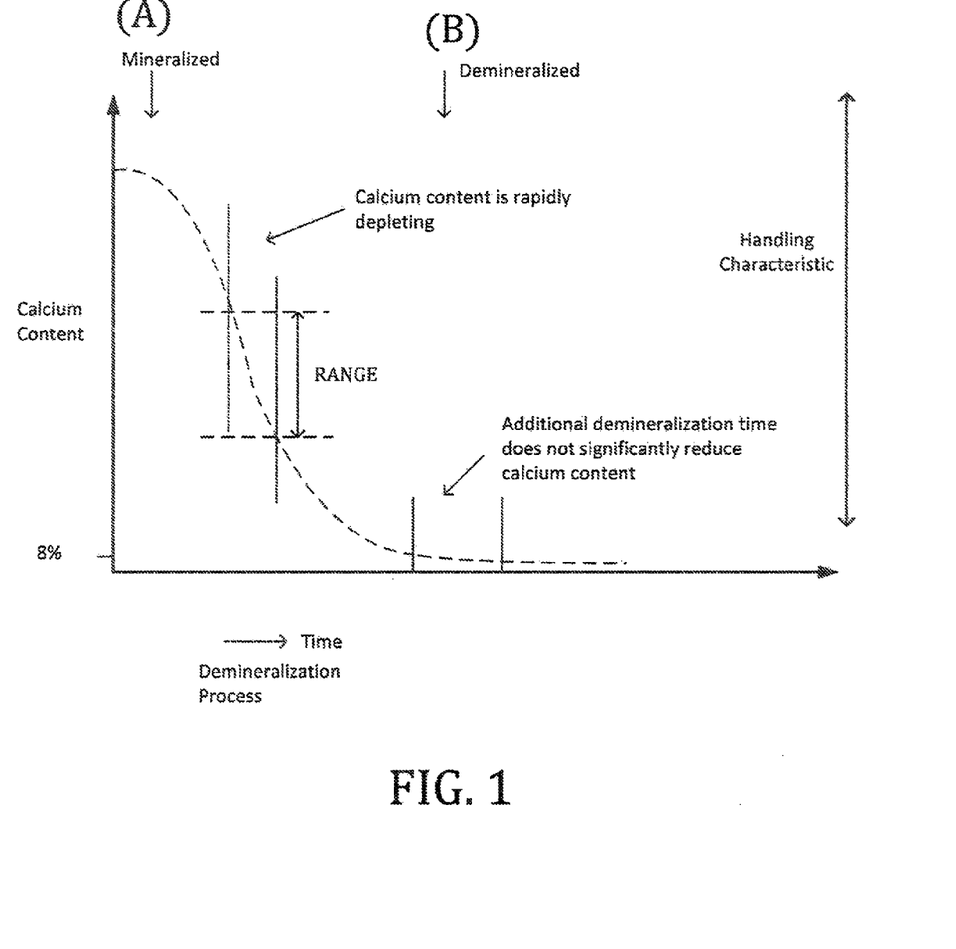
FIG. 1 depicts aspects of bone graft systems and methods according to embodiments of the present invention.

Turning now to the drawings, FIG. 1 depicts aspects of bone composite systems and methods according to embodiments of the present invention. As shown here, as a typical demineralization method proceeds, the amount of calcium in the bone is rapidly depleted. What is more, the acid concentration used, the duration of the demineralization process, and the process temperature are factors which can operate to impact the residual calcium content in the bone. Moreover, there may be variation in the bone density (e.g. due to donor age and/or bone location) as well as in the bone particle size. Hence, it may be difficult to accurately obtain a partially demineralized bone material having a calcium content which is within the specified range, or that is at a particular desired or selected value within the range.

Exemplary bone allograft compositions as disclosed herein contain a first amount of mineralized bone (A) and a second amount of demineralized bone (B). Hence, the bone allograft composition can have a consistent calcium content. Typically, the demineralized bone is provided as a demineralized bone matrix, or allograft bone which has had inorganic mineral removed, leaving behind the organic collagen matrix. As a result of the demineralization process, the DBM is more biologically active (e.g. BMPs were activated during demineralization process) than non-demineralized bone grafts. Conversely the mechanical or structural integrity properties of demineralized bone may be significantly diminished as compared to mineralized bone.

Typically, cortical bone and cancellous bone are separated from one another, and then demineralized. For example, the cortical bone and cancellous bone can be demineralized in separate batches.

Figure 2:
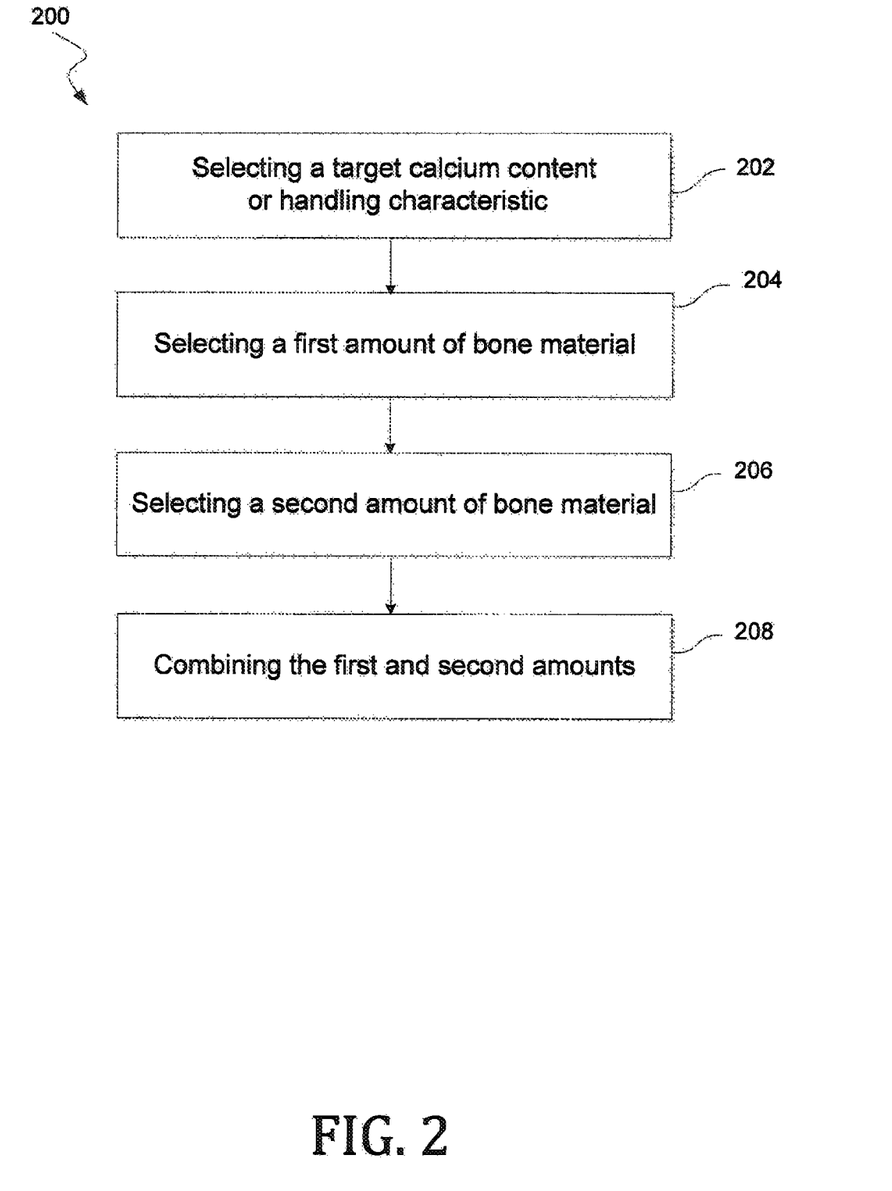
FIG. 2 shows the steps in a method of manufacturing a composite bone graft material according to embodiments of the present invention.

FIG. 2 shows the steps in a method 200 according to embodiments of the present invention. The method 200 may include selecting a target calcium content or handling characteristic 202. The method 200 may include selecting a first amount of bone material 204. In these or other embodiments, the bone material may be non-demineralized bone material from a donor. The method 200 may include selecting a second amount of bone material 206. In some cases, the second amount of bone material may include demineralized bone material. The method 200 may include combining the first and second amounts 208. By combining mineralized and demineralized bone material, it is possible to obtain a resulting mixture having desirable handling characteristics, calcium content, and BMP activity.

In some embodiments, particles sizes and/or volume percentages of components of the bone graft composition may be selected based on handling characteristics of the bone graft composition. Such handling characteristics may include compressibility and cohesion characteristics. Compressibility characteristics for bone graft compositions may include whether the composition is more like sand or more like a sponge. Cohesion characteristics for bone graft compositions may include compositions whether the composition sticks together or does not stick together. Compositions that are more like sand and do not stick together may be difficult for a physician to handle and administer to only the treatment site. Product that is too spongy may be harder for physicians to apply in consistent amounts across different treatments in part because in some instances, a physician may compress the spongy product more than in other instances.

In some cases, composite materials may include components which are present in an amount that is within a volume percentage range. For example, demineralized cancellous bone may be present within a range between about 30% and about 70%, between about 40% and about 60%, between about 45% and about 55%, between about 48% and about 52%, or about 50%. The non-demineralized cancellous bone may be present within a range between about 30% and about 70%, between about 40% and about 60%, between about 45% and about 55%, between about 48% and about 52%, or about 50%. The demineralized cortical bone may be present within a range between about 10% and about 40%, between about 10% and about 30%, between about 15% and about 25%, between about 19% and about 21%, or about 20%. Such volumes may be based on the volume of the bone graft composition product.

The cancellous particles may be more sponge-like and the cortical bone material may reside within spaces of the sponge-like cancellous particles. Hence, the sum of the starting volume amounts may exceed 100% of the final volume of the composite bone material. According to some embodiments, the volume of the final composition may largely be determined by the volumes of demineralized and non-demineralized cancellous components. Hence, a 40 ml volume of demineralized cancellous bone combined with a 40 ml volume of non-demineralized cancellous bone and a 20 ml volume of demineralized cortical bone may provide a composition having a final volume of 80 ml.

In an exemplary embodiment, a composite bone material may have a calcium content within a range from about 10% to about 15%. In these or other embodiments, the bone graft composition may have a calcium content between about 10% and about 19%, between about 12% and about 17%, or about 15%. In some cases, an amount of mineralized cancellous bone present in the composite bone material may have a calcium content of about 20%. In some cases, an amount of demineralized cancellous bone present in the composite bone material may have a calcium content within a range from about 0% (or undetected) to about 8%. In some cases, an amount of mineralized cortical bone present in the composite bone material may have a calcium content of about 25%. In some cases, an amount of cortical demineralized bone present in the composite bone material may have a calcium content within a range from about 0% (or undetected) to about 8%.

Examples of particle sizes of cancellous bone material may include between about 0.1 mm and about 9 mm, between about 2 mm and about 8 mm, between about 1 mm and about 7 mm, between about 1 mm and about 6 mm, between about 1 mm and about 5 mm, between about 0.1 mm and about 4 mm, between about 1 mm and about 4 mm, or between about 0.1 mm and about 1 mm, or between about 0.5 mm and about 4 mm in embodiments. Examples of particles sizes of cortical bone may include between about 100 μm and 2 mm, between about 1 mm and about 2 mm, between about 120 μm and about 710 μm, or between about 100 μm and 1 mm. Smaller particle sizes, including those of cortical bone material, may result in more BMPs being activated. Particle sizes may be obtained using a series of sieves to remove particles smaller and larger than a desired range.

According to some embodiments, instead of adding a patient's own cancellous bone material to an implant graft composition to treat a fracture or other bone defect during a surgical procedure, it is possible to use non-demineralized cancellous bone in a composite bone material as discussed elsewhere herein.

In some cases, the composite bone material will include bone obtained from an allogeneic donor. In some cases, both the demineralized and the mineralized components can be harvested from a common donor and combined to provide the composite bone material. Relatedly, the composite bone material can include cells (e.g. adult mesenchymal stem cells) obtained from the same donor. In some cases, the composite bone material may include bone obtained from a recipient patient. Hence, a composite bone material may include autologous demineralized and/or mineralized bone.

In some embodiments, methods of manufacturing composite bone graft material may include seeding demineralized bone material with a stromal vascular fraction. The stromal vascular fraction may be formed by digesting adipose tissue.

Digesting the adipose tissue may include making a collagenase I solution and filtering the solution, and mixing the adipose solution with the collagenase solution. The adipose solution with the collagenase I solution may be agitated in a shaker flask. This may provide the adipose tissue with a visually smooth appearance. The method may include aspirating a supernatant containing mature adipocytes so as to provide a pellet that is the stromal vascular fraction.

The stromal vascular fraction may include mesenchymal stem cells and other cells, which may be unwanted or unneeded in embodiments of the invention. Unwanted cells may include hematopoietic stem cells and other stromal cells. In these or other embodiments, methods may include incubating the mesenchymal stem cells on the demineralized bone material for a period of time to allow the mesenchymal stem cells to adhere to the demineralized bone material. Methods may include rinsing the seeded demineralized bone material to remove all, substantially all, or a portion of the unwanted cells from the demineralized bone material in embodiments. Methods involving mesenchymal stem cells may be as disclosed in Ser. No. 12/612,583 filed Nov. 4, 2009 and U.S. Provisional Patent Application No. 61/790,412 filed Mar. 15, 2013, the entire content of both is incorporated herein by reference for all purposes.

In some cases, the bone graft composition may be administered to a patient as a flowable, syringeable, putty-like material. For example, a putty-like moldable matrix can be delivered through a cannula or other syringe attachment to a treatment site. Such bone matrix compositions may be used as how soft tissue matrix compositions are used and formed in U.S. patent application Ser. No. 13/712,295 filed Dec. 12, 2012, the entire content of which is incorporated herein by reference for all purposes. In some cases, the bone material and/or mesenchymal stem cells may be present in a morselized form. Hence, compositions and methods as disclosed herein may include a soft tissue or skin matrix material combined with stem cell morsels, so as to form a bone putty. A putty formulation may have good handling characteristics. For example, such morsels or putty compositions may stay in place upon implantation. Relatedly, such morsels or putty compositions may persist at the site of the application (e.g., bone defect area) and resist removal by irrigation and/or contact with blood. In some instances, flowable decellularized skin or de-epidermilized skin (or other soft tissue) can provide and effective carrier to hold demineralized bone material and/or mesenchymal stem cells in place and prevent their migration.

Embodiments of the present invention may encompass delivering the bone graft composition combined with a carrier to a treatment site of the patient. In some cases, the carrier is derived from a human donor and includes an organic phase of a decellularized adipose tissue that has been exposed to alkaline organic solution. Such methods and compositions may be similar to those taught in U.S. patent application Ser. No. 13/970,324 filed Aug. 19, 2013, the entire content of which is incorporated herein by reference for all purposes. In these or other embodiments, methods may include administering treatment material combined with a matrix to a treatment site of a patient. The matrix may include a processed organic phase of decellularized adipose tissue that is substantially free of a stromal vascular fraction. In some cases, the adipose component includes an adipose derived carrier.

Figure 3:
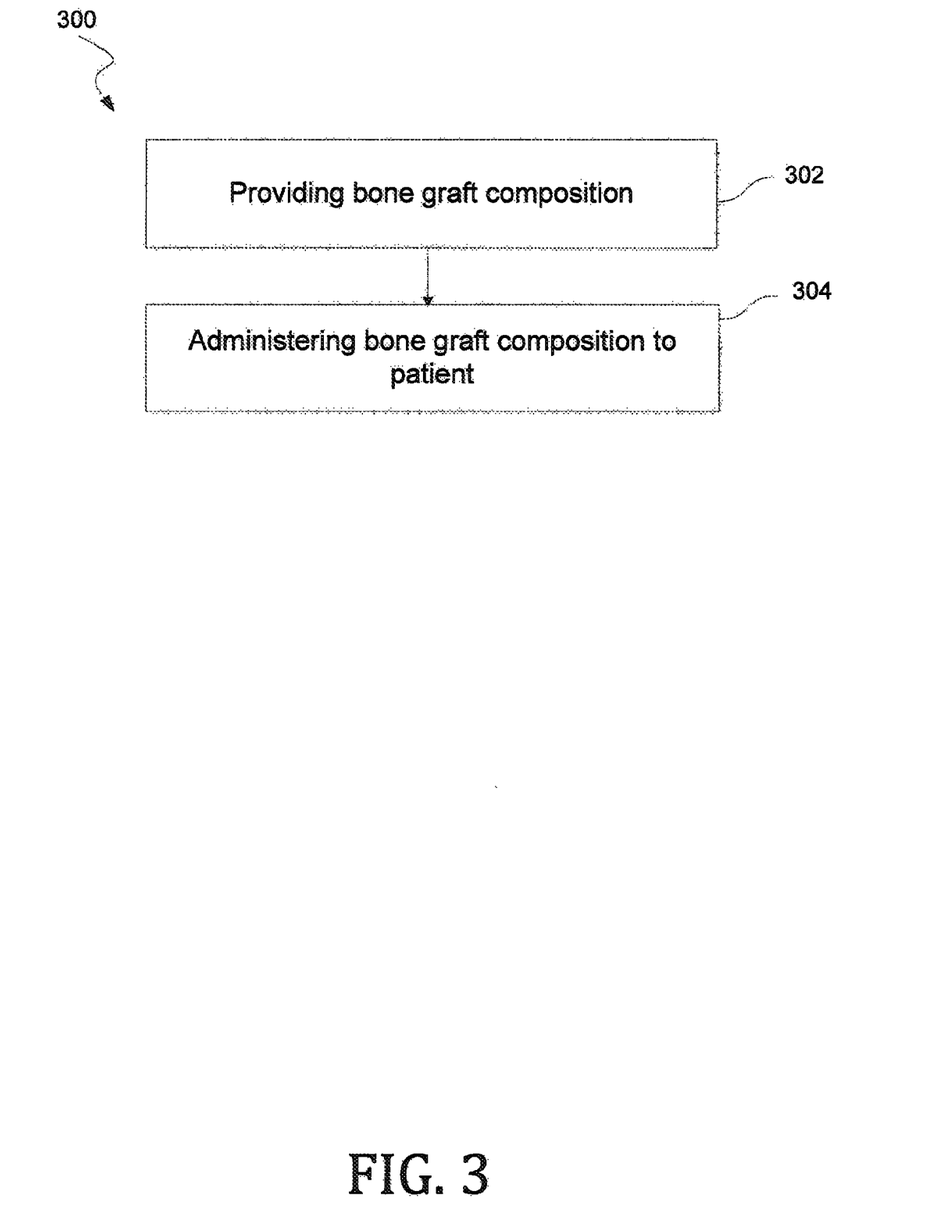
FIG. 3 shows the steps in a method of treating a patient according to embodiments of the present invention.

FIG. 3 shows an method 300 of treating a bone defect in a patient according to embodiments. The method 300 may include providing a bone graft composition 302. In these or other embodiments, the bone graft composition may include any of the bone graft compositions described herein. The method 300 may include administering the bone graft composition to the patient 304.

Example 1

Figure 4:
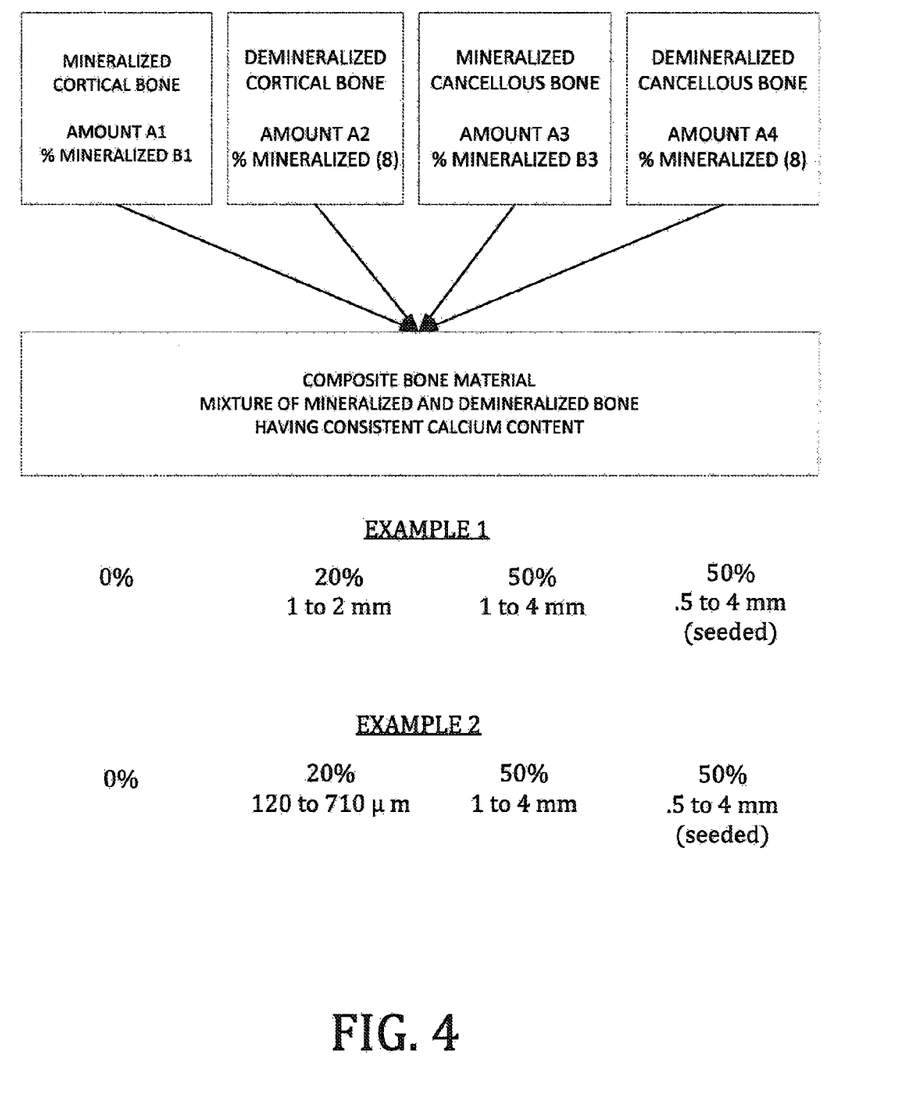
FIG. 4 depicts aspects of bone graft systems and methods according to embodiments of the present invention.

In one example (FIG. 4), a composite bone material includes 50% fully demineralized cancellous bone (e.g. 0.5 mm to 4 mm particle size) seeded with cells (e.g. adult mesenchymal stem cells), 50% non-demineralized cancellous bone (e.g. 1 mm to 4 mm particle size), and 20% fully demineralized cortical bone (e.g. 1 mm to 2 mm particle size). Particle size ranges may be obtained by using two sieves to separate out ground bone material. According to some embodiments, the fully demineralized cortical bone may not contribute toward the final volume of the composite bone material, because the particle size is relatively small and can fill into pores of the larger cancellous particles.

Example 2

In another example (FIG. 4), a composite bone material includes 50% fully demineralized cancellous bone (e.g. 0.5 mm to 4 mm particle size) seeded with cells (e.g. adult mesenchymal stem cells), 50% non-demineralized cancellous bone (e.g. 1 mm to 4 mm particle size), and 20% fully demineralized cortical bone (e.g. 120 µm to 710 µm particle size). According to some embodiments, the fully demineralized cortical bone may not contribute toward the final volume of the composite bone material, because the particle size is relatively small and can fill into pores of the larger cancellous particles.

In each of these examples, it was observed that the allograft material exhibited consistent and satisfying handling characteristics. Hence, by combining a fully demineralized bone material (e.g. DBM) with a non-demineralized bone matrix material, it is possible to create a very consistent partially demineralized bone product, which may otherwise be difficult to produce using traditional demineralization approaches Relatedly, the product can have a consistent calcium content.

Table 1 describes certain characteristics of various composite bone material formulations according to embodiments of the present invention. Each of the formulations in Table 1 includes 20% by volume of demineralized cortical bone.

TABLE 1

| Ratio in product: demineralized cancellous bone to non-demineralized cancellous bone | Calcium content in product (e.g. amount of calcium present in mixture) | Handling Characteristics of product (description) |
| --- | --- | --- |
| 0:1 (0% demin) | 25% | Hard sand like particles, does not stick together well |
| 1:4 (25% demin) | 19% | Sand like particles, does not stick together well |
| 1:1 (50% demin) | 15% | Sticks together very well, not too hard, not too spongy |
| 3:4 (75% demin) | 10% | Sticks together well, slightly spongy |
| 1:0 (100% demin) | less than 8% | Does not stick together well, very spongy |

According to some embodiments, bone graft material can be demineralized for 60 minutes in 1 N HCl during the process. To evaluate residual calcium content, samples of the morselized bone product were subjected to inductively coupled plasma spectroscopy analysis by SunLabs (Tampa, Fla.). The resulting residual calcium was 1.0%. Each value is well below the 8.0% residual calcium required by AATB to claim full demineralization.

To evaluate certain characteristics of composite bone material, samples were manipulated by hand. For example, by squeezing or holding the material in the hand, it is possible to observe adhesion characteristics, for example by noting the extent to which the material sticks to one's fingers when extending the fingers. Similarly, by squeezing or holding the material in the hand, it is possible to observe cohesion characteristics, for example by noting the extent to which the material tends to adhere to itself. Further, by squeezing or holding the material in the hand, it is possible to observe compressibility characteristics, for example by noting the extent to which the material can be compressed. What is more, by squeezing or holding the material in the hand, it is possible to observe abrasiveness characteristics, for example by noting the shape and/or hardness of particles present in the material.

When referring to the calcium content in the product, there may be various types of calcium, such as calcium phosphate, calcium carbonate, and the like. For example, some bone material is formed mostly of calcium phosphate in the chemical arrangement termed calcium hydroxylapatite.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included.

What is claimed is:

1. A method of manufacturing a composite bone graft material for administration to a treatment site of a patient, the method comprising:
    selecting a target calcium content or handling characteristic of the composite bone graft material;
    obtaining a first amount of non-demineralized donor bone material;
    obtaining a second amount of demineralized donor bone material;
    obtaining a third amount of demineralized donor bone material; and
    combining the first amount, second amount, and third amount of donor bone material so as to obtain a bone graft composition having the target calcium content or handling characteristic, wherein:
    the first amount, the second amount, and the third amount are sourced from a common donor,
    the first amount of non-demineralized donor bone material comprises cancellous bone,
    the second amount of demineralized donor bone material comprises cancellous bone and comprises between about 50% and about 75% of the final volume of the bone graft composition, and
    the third amount of demineralized donor bone material comprises cortical bone, and
    the calcium content of the bone graft composition is between about 10% and about 15%.

2. The method according to claim 1, wherein prior to the combining step, the method further comprises seeding mesenchymal stem cells onto the second amount of demineralized donor bone material.

3. The method according to claim 1, wherein the first amount comprises particles having sizes between about 1 mm and about 4 mm.

4. The method according to claim 1, wherein the second amount comprises particles having sizes between about 0.5 mm and about 4 mm.

5. The method according to claim 1, wherein the third amount comprises particles having sizes between about 1 mm and about 2 mm.

6. The method according to claim 1, wherein the third amount comprises particles having sizes between about 120 μm and about 710 μm.

7. The method according to claim 1, wherein:
    the first amount comprises about 50% of the final volume of the bone graft composition, and
    the second amount comprises about 50% of the final volume of the bone graft composition.

8. The method according to claim 1, wherein:
    the first amount comprises about 50% of the final volume of the bone graft composition,
    the second amount comprises about 50% of the final volume of the bone graft composition, and the third amount comprises about 20% of the final volume of the bone graft composition.

9. The method according to claim 1, wherein the first amount comprises between about 25% and about 50% of the final volume of the bone graft composition.

10. The method according to claim 1, wherein the third amount comprises between about 19% and about 21% of the final volume of the bone graft composition.

11. The method according to claim 1, wherein the third amount comprises about 20% of the final volume of the bone graft composition.

12. The method according to claim 1, wherein:
the first amount comprises particles having sizes between about 1 mm and about 4 mm,
the second amount comprises particles having sizes between about 0.5 mm and about 4 mm, and
the third amount comprises particles having sizes between about 120 μm and about 710 μm.

13. The method according to claim 1, wherein the selecting step comprises selecting the target calcium content of the composite bone material.

14. The method according to claim 1, wherein the selecting step comprises selecting the handling characteristic of the composite bone material.

* * * * *